United States Patent [19]

Fleet

[11] Patent Number: 4,894,388

[45] Date of Patent: Jan. 16, 1990

[54] GLYCOSIDASE INHIBITORS AND USE THEREOF

[75] Inventor: George W. J. Fleet, Oxford, United Kingdom

[73] Assignee: Monsanto Company, St. Louis, Mo.

[21] Appl. No.: 288,735

[22] Filed: Dec. 22, 1988

[51] Int. Cl.$^4$ .................... C07D 207/12; A61K 31/40
[52] U.S. Cl. ..................................... 574/425; 548/556
[58] Field of Search ......................... 548/556; 514/425

[56] References Cited

U.S. PATENT DOCUMENTS 3,312,716  4/1967  Biel et al. .............................. 548/556

OTHER PUBLICATIONS

Molyneax et al., Arch. Biochem. Biophys. 251, 450–457 (1986).
Elbein, Biochemistry 26, 2502–2510 (1987).
Schweden et al., Eur. J. Biochem. 157, 563–570 (1986).
Hettkamp et al., Eur. J. Biochem. 142, 85–90 (1984).
Fleet and Son, Tetrahedron 44, 2637–2647 (1988).

*Primary Examiner*—David B. Springer
*Attorney, Agent, or Firm*—Scott J. Meyer; James W. Williams, Jr.

[57] ABSTRACT

The specificity of glycosidase inhibitory activity of the novel 1,4-dideoxy-1,4-imino-L-allitol is substantially changed by substituting the ring nitrogen with an alkyl or benzyl substituent.

7 Claims, 1 Drawing Sheet

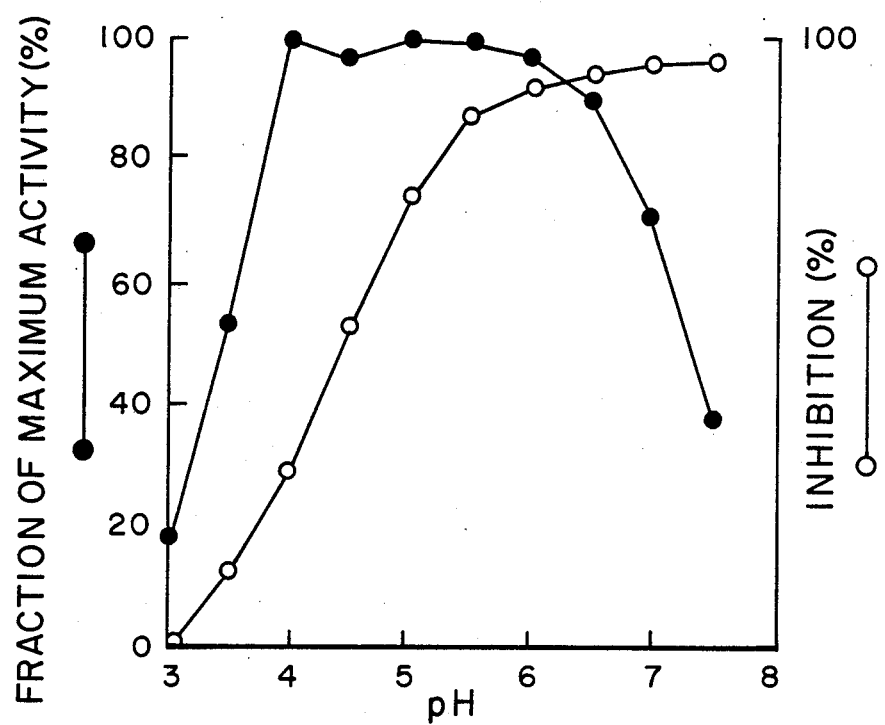

GLYCOSIDASE INHIBITORS AND USE THEREOF

BACKGROUND OF THE INVENTION

This invention relates to 1,4-dideoxy-1,4-imino-L-allitol and N-substituted derivatives thereof which have glycosidase inhibitory activity. More particularly, the invention relates to a method of substantially changing the specificity of glycosidase inhibitory activity of 1,4-dideoxy-1,4-imino-L-allitol by substitution of the ring nitrogen without altering the chirality of hydroxyl groups.

It is known that polyhydroxylated pyrrolidines and piperidines provide an extensive class of powerful and specific glycosidase inhibitors. See, for example, Scofield et al., *Life Sci.* 39, 645-650 (1986); Elbein, *Ann. Rev. Biochem.* 56, 497-534 (1987); and Fleet et al., *FEBS Lett.* 237, 128-132 (1988). Several of these glycosidase inhibitors have been found to inhibit human immunodeficiency virus (HIV) synctium formation and virus replication, thereby indicating their potential use as antiretroviral agents. Three such compounds thus suggested as potential anti-AIDS drugs are castanospermine, 1-deoxynojirimycin (DNJ) and 2,5-dihydroxymethyl-3,4-dihydroxypyrrolidine (DMDP). See, for example, Sunkara et al., *Biochem. Biophys. Res. Commun.* 148 (1), 206-210 (1987); Tyms et al., *Lancet*, Oct. 31, 1987, pp. 1025-1026; Walker et al., *Proc. Natl. Acad. Sci. USA* 84, 8120-8124 (1987); and Gruters et al., *Nature* 330, 74-77 (1987). Although the effects of these compounds may arise from their properties as specific glycosidase inhibitors, it has been shown that not all glycosidase I inhibitors are effective inhibitors of HIV as reported by Fleet et al., *FEBS Lett.* 237, 128-132 (1988).

Despite attempts to predict the specificity of inhibition of some of these compounds from their structure, the structural features necessary for the inhibition of a particular glycosidase cannot readily be defined. Among the factors that may determine specificity are the number and chirality of the hydroxyl groups, the ring structure and substitution of the ring nitrogen. Thus, it has been reported that alteration of the chirality of a hydroxyl group on a polyhydroxylated alkaloid generally changes the specificity of inhibition. See Molyneux et al., *Arch. Biochem. Biophys.* 251, 450-457 (1986); and Elbein et al., *Biochemistry* 26, 2502-2510 (1987). Substitution of the ring nitrogen atom usually decreases the inhibitory capacity of an alkaloid [Schweden et al., *Eur. J. Biochem.* 157, 563-570 (1986)] but has been shown in one case to enhance inhibition [Hettkamp et al., *Ibid.* 142, 85-90 (1984)]. Therefore, the actual effectiveness of a given compound as a glycosidase inhibitor or the effect on specificity by a given structural change of the compound are unpredictable.

BRIEF DESCRIPTION OF THE INVENTION

In accordance with the present invention the novel compound, 1,4-dideoxy-1,4-imino-L-allitol, and N-substituted derivatives thereof which have glycosidase inhibitory activity are provided. The N-substituents can be alkyl having from one to about six carbon atoms or benzyl. N-substituted derivatives were synthesized which unexpectedly have substantially different properties in specificity of glycosidase inhibition than that exhibited by the underivatized parent compound, 1,4-dideoxy-1,4-imino-L-allitol.

1,4-dideoxy-1,4-imino-L-allitol (DIA) is a moderately strong inhibitor of multiple forms of human liver α-D-mannosidase but it also inhibits α-L-fucosidase, β-D-glucosidase, N-acetyl-β-hexosaminidase and β-D-mannosidase to a lesser extent. In accordance with a preferred embodiment of the invention, methylation of the ring nitrogen in DIA markedly decreased inhibition of all the glycosidases except N-acetyl-β-D-hexosaminidase; whereas, N-benzylation of DIA essentially abolished all inhibitory activity except towards α-L-fucosidase, which is more strongly inhibited than either DIA or the N-methyl derivative of DIA. These changes in specificity were unexpected particularly in view of their dissimilarity and since they do not result from alteration in structure involving chirality of the hydroxyl groups.

The structures of these novel inhibitory compounds can be conveniently shown in their HCl salt forms as follows:

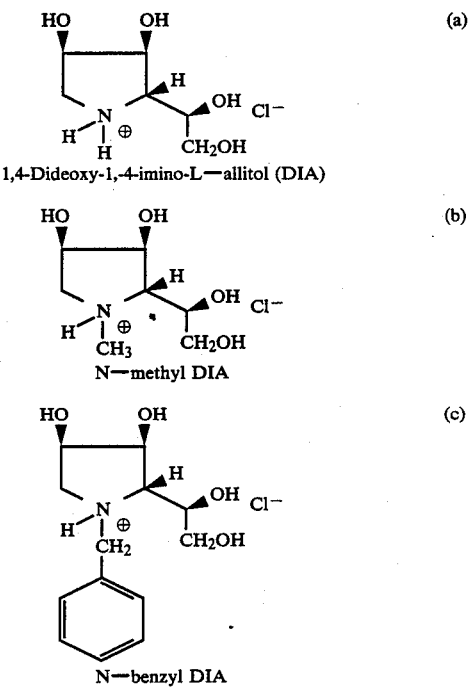

DETAILED DESCRIPTION OF THE INVENTION

While the specification concludes with claims particularly pointing out and distinctly claiming the subject matter regarded as forming the present invention, it is believed that the invention will be better understood from the following detailed description of preferred embodiments of the invention taken in conjunction with the appended drawing, in which:

FIG. 1 is a graphical representation which shows the inhibition of α-L-fucosidase by the N-benzyl derivative of 1,4-dideoxy-1,4-imino-L-allitol. α-L-Fucosidase activity was measured in the presence and absence of said inhibitor compound. The fraction of activity lost in the presence of the inhibitor was calculated for each pH; ●=α-L-fucosidase activity; o=inhibition (%).

The synthesis of the underivatized parent compound, 1,4-dideoxy-1,4-imino-L-allitol (DIA), can be carried out by a method substantially analogous to that used to synthesize the corresponding D-enantiomer from D- gulonolactone as described by Fleet and Son, *Tetrahedron* 44, 2637–2647 (1988), the disclosure of which is incorporated herein by reference. In accordance with the synthesis method as modified herein to produce the L-enantiomer, 1,4-dideoxy-1,4-imino-L-allitol can be prepared in six steps from L-gulonolactone, and readily converted to the HCl salt form in a seventh step, as follows:

Synthesis of DIA

The starting material, L-gulonolactone, is a commercially available compound.

(1) L-Gulonolactone is treated with acetone and dimethylpropane to give the lactone, 2,3:5,6-di-O-isopropylidene-L-gulonolactone.

(2) The di-O-isopropylidene derivative is reduced with lithium aluminum hydride to afford the diol, 2,3:5,6-di-O-isopropylidene-L-gulitol.

(3) The hydroxyl groups in the diol are esterified with methanesulfonyl chloride to form the dimesylate, 1,4-bis(methanesulfonyl)-2,3:5,6-di-O-isopropylidene-L-gulitol.

(4) The dimesylate is reacted with benzylamine to undergo cyclisation and give the amine (protected pyrrolidine), N-benzyl-1,4-dideoxy-2,3:5,6-di-O-isopropylidene-1,4-imino-L-allitol.

(5) The protected pyrrolidine is subjected to hydrogenolytic removal of the benzyl group to provide the acetonide, 1,4-dideoxy-2,3:5,6-di-O-isopropylidene-1,4-imino-L-allitol, which was recovered as a yellow oil, $[\alpha]_D^{20} - 35°$ (c, 1.26 in CHCl$_3$).

(6) The protecting groups in the acetonide are removed by hydrolysis with aqueous trifluoroacetic acid (TFA) to give, after treatment with aqueous NaOH and purification by ion exchange chromatography, 1,4-dideoxy-1,4-imino-L-allitol.

(7) The resulting free base is dissolved in water and adjusted to pH 4 with dilute HCl to give, after freeze drying, 1,4-dideoxy-1,4-imino-L-allitol hydrochloride, m.p. 112°–113° C., $[\alpha]_D^{20} - 24.6°$ (c, 1.12 in H$_2$O).

The N-alkyl derivatives of 1,4-dideoxy-1,4-imino-L-allitol can be prepared in a two step process from the amine prepared in step 5, above, and readily converted to the HCl salt form in a third step, as described in the following illustrative method for the synthesis of the N-methyl derivative. Other N-alkyl derivatives can be prepared in an analogous manner, for example, by butylation or hexylation, instead of methylation as described in this example.

Synthesis of N-Alkyl Derivatives of DIA (1) 1,4-Dideoxy-2,3:5,6-di-O-isopropylidene-1,4-imino-L-allitol is hydrogenated together with a threefold excess of aqueous formaldehyde in methanol in the presence of palladium black to give N-methyl-1,4-dideoxy-2,3:5,6-di-O-isopropylidene-1,4-imino-L-allitol, an oil, $[\alpha]_D^{20} 0.0°$ (C, 1.01 in CHCl$_3$).

(2) The protecting groups in the resulting diacetonide are removed by hydrolysis with aqueous TFA to give, after purification by ion exchange chromatography, N-methyl-1,4-dideoxy-1,4-imino-L-allitol.

(3) The resulting free amine is dissolved in water and adjusted to pH 4 with dilute HCl to afford, after freeze drying, the readily crystallizable N-methyl-1,4-dideoxy-1,4-imino-L-allitol hydrochloride, m.p. 140°–141° C., $[\alpha]_D^{20} + 1.8°$ (C, 1.05 in H$_2$O).

The N-benzyl derivative of 1,4-dideoxy-1,4-imino-L-allitol can be prepared in essentially a one step method from the fully protected amine prepared in step of the DIA synthesis method, above, and readily converted to the HCl salt form in a second step, as follows:

Synthesis of N-Benzyl Derivative of DIA (1) N-Benzyl-1,4-dideoxy-2,3:5,6-di-O-isopropylidene-1,4-imino-L-allitol is treated with aqueous TFA at room temperature to remove the protecting groups to give N-benzyl-1,4-dideoxy-1,4-imino-L-allitol.

(2) The resulting free amine is dissolved in water and adjusted to pH 4 with dilute HCl to give, after freeze drying, N-benzyl-1,4-dideoxy-1,4-imino-L-allitol hydrochloride, m.p. 110°–111° C., $[\alpha]_D^{20} - 25.5°$ (c, 1.07 in H$_2$O).

The following detailed examples will further illustrate the invention although it will be appreciated that the invention is not limited to these specific examples.

EXAMPLE 1

A. 2,3:5,6-Di-O-isopropylidene-L-gulonolactone m.p. 155° C. (from ethyl acetate) $[\alpha]_D^{20} - 76.6°$ (c, 1.99 in CHCl$_3$), was prepared from L-gulonolactone in 85% yield as previously described by Fleet in copending application Ser. No. 249,153, filed Sept. 26, 1988. According to this method, the title compound is synthesized by treatment of L-gulonolactone with acetone and 2,2-dimethoxypropane and a catalytic amount of p-toluenesulfonic acid under dry nitrogen for 36 hours (h) followed by stirring with an excess of sodium bicarbonate, removing the solvent under reduced pressure, dissolving the residue in dichloromethane, washing with water, drying the organic extracts (MgSO$_4$), removing the solvent under reduced pressure and recrystallizing from ethyl acetate to give a white crystalline solid.

B. 2,3:5,6-Di-O-isopropylidene-L-gulitol

The lactone prepared in step A (15.00 g, 58.1 mmol) was added to a stirred solution of lithium aluminum hydride (4.42 mg, 116 mmol) in tetrahydrofuran:ether, 8:1, (210 ml) at room temperature. After 60 min, the excess hydride was destroyed by addition of water (10 ml) and the reaction mixture was partitioned between brine (150 ml) and ethyl acetate (250 ml). The organic layer was dried (magnesium sulphate), filtered and the solvent removed in vacuo to give a syrup which was purified by flash chromatography (ethyl acetate:hexane, 1:1) to give 2,3:5,6-di-O-isopropylidene-L-gulitol, (14.0 g, 97%), m.p. 73°–75° C. (from ether $[\alpha]_D^{20} - 11.0°$ (c, 2.32 in CHCl$_3$). $\nu_{max}$ (KBr) 3500–3100 cm$^{-1}$ [lit* data for D enantiomer m.p. 73°–75° C. (from ether) $[\alpha]_D^{20} + 11.3°$ (c, 1.80 in CHCl$_3$)].

C. 1,4-Bis(methanesulphonyl)-2,3:5,6-di-O-isopropylidene-L-gulitol

Methane sulphonyl chloride (7.0 ml, 90.4 mmol) and a catalytic amount of 4,4-dimethylaminopyridine (0.40 g) were added to a stirred solution of the diol from step B (6.00 g, 22.9 mmol) in pyridine (60 ml) and the reaction mixture stirred for 2 h at 0° C. The reaction was quenched with water (5 ml) and the reaction mixture was then evaporated to give a residue which was dissolved in chloroform (200 ml); the chloroform solution was washed with water, dried (magnesium sulphate) and the solvent removed to give an oil which was purified by flash chromatography (2:1, ethyl acetate:hexane) to afford 1,4-bis-(methanesulphonyl)-2,3:5,6-di-O-isopropylidene-L-gulitol, colorless syrup, (7.56 g, 100% yield, $[\alpha]_D^{20} + 7.3°$ (c, 1.37 in CHCl$_3$). $\nu_{max}$ (neat) 1350 cm$^{-1}$. [lit* data for D enantiomer, colorless oil, $[\alpha]_D^{20}$ 7.3° (c, 1.82 CHCl$_3$)].

D. N-Benzyl-1,4-dideoxy-2,3:5,6-di-O-isopropylidene-1,4-imino-L-allitol

The dimesylate from step C (7.50 g, 27.9 mmol) in benzylamine (25 ml) was warmed at 60°-70° C. for 60 h. The benzylamine was removed in vacuo and the residue was then dissolved in brine (50 ml) and extracted with chloroform (2×50 ml). The combined organic extracts were washed with water (2×50 ml), dried (magnesium sulphate) and the solvent removed to give, after purification by flash chromatography, (2:3, ether:hexane), N-benzyl-1,4-dideoxy-2,3:5,6-di-isopropylidene-1,4-imino-L-allitol, colorless oil (5.10 g, 85% yield), $[\alpha]_D^{20} + 12.5°$ (c, 1.76 in $CHCl_3$). [lit* data for D enantiomer, colorless oil, $[\alpha]_D^{20} - 12.2°$ (c, 1.07 in $CHCl_3$)].

E. 1,4-Dideoxy-2,3:5,6-di-O-isopropylidene-1,4-imino-L-allitol

The cyclized tertiary amine from step D (1.10 g, 3.30 mmol) in ethanol (50 ml) was stirred under an atmosphere of hydrogen in the presence of palladium black (700 mg) at room temperature for 4 h. The reaction mixture was filtered through celite to remove the catalyst and the solvent then removed to give, after purification by flash chromatography (ethyl acetate:hexane, 3:1), 1,4-dideoxy-2,3:5,6-di-O-isopropylidene-1,4-imino-L-allitol, (665 mg, 83%), pale yellow oil, $[\alpha]_D^{20} -35.2°$ (c, 1.26 in $CHCl_3$), $v_{max}$ (neat) 3320 (w, NH) $cm^{-1}$. [lit* data for D enantiomer, pale yellow oil, $[\alpha]_D° +34.1°$ (c, 0.41 in $CHCl_3$)].

F. 1,4-Dideoxy-1,4-imino-L-allitol Hydrochloride

The acetonide (330 mg, 1.36 mmol) in 50% aqueous trifluoroacetic acid (20 ml) was stirred at room temperature for 14 h. The solvent was removed; the resulting trifluoroacetate salt was neutralized with dilute aqueous sodium hydroxide and purified by ion exchange chromatography (Dowex 50 X, 8-100, H+ form, eluted with 0.5 molar aqueous ammonium hydroxide) to give 1,4-dideoxy-1,4-imino-L-allitol; the free base was dissolved in water (5 ml) and the solution was adjusted to pH 4 with dilute aqueous hydrochloric acid to afford, after freeze drying, 1,4-dideoxy-1,4-imino-L-allitol hydrochloride, (259 mg, 96%), m.p. 112°-113° C., $[\alpha]_D^{20} -24.6°$ (c, 1.12 in $H_2O$), $v_{max}$(KBr) 3600-3200 (br, NH and OH) $cm^{-1}$. [lit* data for D enantiomer, m.p. 110°-111° C., $[\alpha]_D^{20} +29.420$ (c, 0.53 in $H_2O$)].

*=Fleet and Son, *Tetrahedron* 24(9), 2637-2647 (1988).

EXAMPLE 2

A. N-Benzyl-1,4-dideoxy-1,4-imino-L-allitol Hydrochloride

The fully protected amine prepared in step D of Example 1 (630 mg, 1.89 mmol) was stirred at room temperature in 50% aqueous trifluoroacetic acid (20 ml) for 24 h. The solvent was removed; the resulting trifluoroacetate salt was neutralized with dilute aqueous sodium hydroxide and the residue purified by ion exchange chromatography (Dowex 50 X, 8-100, H+ form, eluted with 0.5 molar aqueous ammonium hydroxide) to give N-benzyl-1,4-dideoxy-1,4-imino-L-allitol as a syrup; the free base was dissolved in water (5 ml) and the solution was adjusted to pH 4 with dilute aqueous hydrochloric acid to afford, after freeze drying, N-benzyl-1,4-dideoxy-1,4-imino-L-allitol hydrochloride, (530 mg, 97%), m.p. 155°-156° C., $[\alpha]_D^{20} -25.5°$ (c, 1.07 in $H_2O$), $v_{max}$ (KBr) 3500-3100 (br, NH and OH) $cm^{-1}$. [lit* data for D-enantiomer, hygroscopic solid $[\alpha]_D^{20} +23.1°$ (c, 0.72 in $H_2O$)].

EXAMPLE 3

A. N-Methyl-1,4-dideoxy-2,3:5,6-di-O-isopropylidene-1,4-imino-L-allitol

Aqueous formaldehyde (37% solution, 0.27 ml, 3.33 mmol) was added to a solution of 1,4-dideoxy-2,3:5,6-di-O-isopropylidene-1,4-imino-L-allitol (270 mg, 1.11 mmol) in methanol (20 ml), the resulting reaction mixture was stirred under an atmosphere of hydrogen in the presence of palladium black (50 mg) at room temperature for 12 h when TLC (ethyl acetate) showed no starting material ($R_f$ 0.4) and only one product ($R_f$ 0.2). The reaction mixture was filtered through celite to remove the catalyst and the solvent then removed to give, after purification by flash chromatography (ethyl acetate:hexane, 3:1), N-methyl-1,4-dideoxy-2,3:5,6-di-O-isopropylidene-1,4-imino-L-allitol, (274 mg, 96%), yellow oil, $[\alpha]_D^{20} 0.0°$ (c, 1.01 in $CHCl_3$).

B. N-Methyl-1,4-dideoxy-1,4-imino-L-allitol hydrochloride.

The diacetonide from step A (230 mg, 0.89 mmol) in 50% aqueous trifluoroacetic acid (14 ml) was stirred at room temperature for 24 h. The solvent was removed; the resulting trifluoroacetate salt was neutralized with dilute aqueous sodium hydroxide and purified by ion exchange chromatography (Dowex 50 X, 8-100, H+ form, eluted with 0.5 molar aqueous ammonium hydroxide) to give N-methyl-1,4-dideoxy-1,4-imino-L-allitol; the free base was dissolved in water (5 ml) and the solution was adjusted to pH 4 with dilute aqueous hydrochloric acid to afford, after freeze drying, N-methyl-1,4-dideoxy-1,4-imino-L-allitol hydrochloride, (189 mg, 99%), m.p. 140°-141° C., $[\alpha]_D^{20} + 1.8°$ (c, 1.05 in $H_2O$), $v_{max}$ (KBr) 3600-3100 (br, NH and OH) $cm^{-1}$.

The following example will illustrate the change in specificity of glycosidase inhibitory activity of 1,4-dideoxy-1,4-imino-L-allitol by substitution of the ring nitrogen, although it will be understood that the inhibitory activity of the compounds of the invention is not limited to this specific example.

EXAMPLE 4

Materials and Methods
Tissue

Post mortem human liver, which had been stored at −20° C. until required was homogenized in deionized water (50%, w/v) in a Potter-Elvehjem homogenizer and then centrifuged at 37,000 g for 30 min in an MSE 18 centrifuge. The resultant supernatant was used as the source of enzymic activities.

Enzyme Assays

The glycosidase activities in an extract of normal human liver were assayed by using the appropriate fluorigenic 4-methylumbelliferyl glycoside substrate (Koch-Light, Haverhill, Suffolk, U.K.) with a concentration of 0.5 mM at the optimal pH of each enzyme [Burditt et al., *Clin. Chim. Acta* 140, 201-209 (1980)]. Human liver acidic (lysomal) and neutral (cystosolic) α-D-mannosidases were assayed similarly at their pH-optima, of 4.0 and 6.5, respectively, after separation by affinity chromatography on concanavalin A-Sepharose ® (Pharmacia Ltd, Milton Keynes, Bucks, U.K.) [Phillips et al., *Biochem. J.* 153, 579-587 (1976)]. The residual intermediate (Golgi) α-mannosidase II activity in extracts of fibroblasts from a patient with the lysosomal storage disease, mannosidosis, was assayed at pH 5.75 using the synthetic substrate (Burditt et al, Ibid.). The specificity of the inhibitors was determined by assaying the glycosidases in the presence and absence of a 1 mM solution of each compound. The nature of the inhibition and the value of $K_i$ were determined using the Dixon graphical procedure.

RESULTS

Inhibition of multiple forms of α-D-mannosidase

DIA is a good inhibitor of lysosomal α-D-mannosidase with a value of $K_i$ of $1.7 \times 10^{-4}$M at its pH optimum of 4.0. It is also a potent inhibitor of the processing enzyme, α-D-mannosidase II, and to a lesser extent of the neutral cytosolic α-D-mannosidase (Table 1). Methylation of the ring nitrogen decreased markedly the inhibition of all three forms of α-D-mannosidase. N-benzylation almost completely eliminated the inhibition of all three α-D-mannosidases. This suggests that the introduction of a group on the ring nitrogen prevents the binding of the inhibitor to the active sites of the enzymes.

Specificity of Inhibition of other glycosidases

N-methylation of DIA also decreased the inhibition of α-L-fucosidase and β-D-mannosidase but did not appreciably alter its effect on hexosaminidase (Table 1). In contrast, N-benzylation of DIA markedly decreased or abolished the inhibition of β-D-mannosidase and hexosaminidase but enhanced the inhibition of α-L-fucosidase. This was a highly selective phenomenon as no other glycosidases were inhibited by more than 15% by this compound.

The inhibition of α-L-fucosidase by N-benzyl DIA was competitive with a $K_i$ value of $5 \times 10^{-5}$ at pH 5.5. It was also pH-dependent (FIG. 1) with the inhibition appearing to increase with the ionization of a group with a pK of approximately 4.5. N-Benzyl-DIA is a basic compound and would be protonated over the pH-range used for inhibition studies. Therefore it was concluded that this effect was due to the ionization of a group, probably a carboxyl group on the enzyme. Two carboxyl groups have been implicated in the catalytic mechanism [White et al., *Biochim. Biophys. Acta.* 829, 303–310 (1985)] and active-site inactivation [White et al., Ibid. 873, 198–203 (1986)] of human liver α-L-fucosidase.

TABLE 1.

Inhibition of Human Liver Glycosidases

Enzymic activities were measured in the presence and absence of 1 mM inhibitor. Inhibition (%) was calculated as the fraction of activity lost in the presence of inhibitor. The values are means of two to four independent determinations.

| Enzyme | Inhibition (%) | | |
|---|---|---|---|
| | DIA | N—methyl DIA | N—benzyl DIA |
| α-D-Mannosidase | | | |
| Lysosomal (acidic) | 84 | 13 | 3 |
| Golgi II | 95 | 33 | 0 |
| Cytosolic (neutral) | 61 | 20 | 4 |
| β-D-Mannosidase | 14 | 4 | 0 |
| α-L-Fucosidase | 60 | 28 | 74 |
| β-N acetyl hexosaminidase | 42 | 37 | 15 |

Various other examples will be apparent to the person skilled in the art after reading the present disclosure without departing from the spirit and scope of the invention. It is intended that all such other examples be included within the scope of the appended claims.

What is claimed is:

1. A compound selected from the group consisting of 1,4-dideoxy-1,4-imino-L-allitol and its N-substituted alkyl and benzyl derivatives and the pharmaceutically acceptable acid salts thereof in which the alkyl group contains from one to six carbon atoms.

2. 1,4-Dideoxy-1,4-imino-L-allitol or its HCl salt.

3. N-Methyl-1,4-dideoxy-1,4-imino-L-allitol or its HCl salt.

4. N-Benzyl-1,4-dideoxy-1,4-imino-L-allitol or its HCl salt.

5. 1,4-Dideoxy-2,3:5,6-di-O-isopropylidene-1,4-imino-L-allitol.

6. The method of substantially changing the specificity of glycosidase inhibitory activity of 1,4-dideoxy-1,4-imino-L-allitol or its HCl salt consisting essentially of substituting the ring nitrogen with an alkyl substituent in which the alkyl group contains from one to six carbon atoms.

7. The method of substantially changing the specificity of glycosidase inhibitory activity of 1,4-dideoxy-1,4-imino-L-allitol or its HCl salt from predominantly an inhibitor of α-D-mannosidase to one that selectively inhibits α-L-fucosidase consisting essentially of substituting the ring nitrogen with a benzyl group.

* * * * *

UNITED STATES PATENT AND TRADEMARK OFFICE
CERTIFICATE OF CORRECTION

PATENT NO. : 4,894,388

DATED : January 16, 1990

INVENTOR(S) : George W. J. Fleet

It is certified that error appears in the above-identified patent and that said Letters Patent is hereby corrected as shown below:

In col. 2, line 64, insert "●" before --α-fucosidase activity--.
In col. 3, line 68, insert "4" after --step--. In col. 5, line 44, "29.420" should read --29.4°--. In col. 5, line 45, "24" should read --44--. In col. 6, line 57, "140" should read --104--.

Signed and Sealed this

Thirtieth Day of October, 1990

Attest:

HARRY F. MANBECK, JR.

Attesting Officer

Commissioner of Patents and Trademarks